United States Patent [19]

Broussard

[11] 4,273,530
[45] Jun. 16, 1981

[54] ORTHODONTIC APPLIANCE AND CLASP THEREFOR

[76] Inventor: Garfford J. Broussard, 203 Chimney Rock, Houston, Tex. 77024

[21] Appl. No.: 39,798

[22] Filed: May 17, 1979

[51] Int. Cl.³ .............................................. A61C 7/00
[52] U.S. Cl. .................................................... 433/6
[58] Field of Search ...................... 433/6, 7, 18, 20, 22

[56] References Cited

U.S. PATENT DOCUMENTS

| 3,967,379 | 7/1976 | Bergersen | 433/6 |
| 3,987,547 | 10/1976 | Moss | 433/18 |

*Primary Examiner*—Robert Peshock
*Attorney, Agent, or Firm*—Arnold, White & Durkee

[57] ABSTRACT

An orthodontic appliance which includes a plurality of clasps, wherein each clasp has a hook and eye portion for removably mounting the appliance in the mouth of the patient.

6 Claims, 7 Drawing Figures

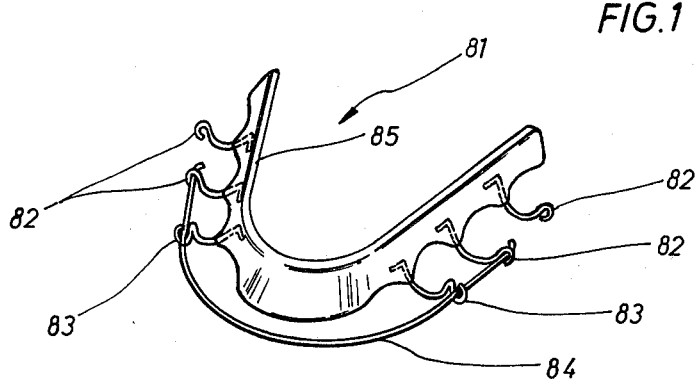
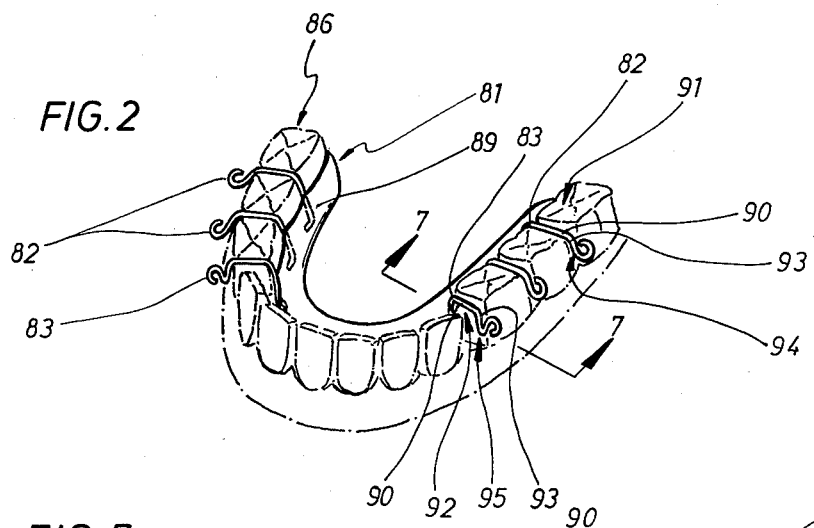
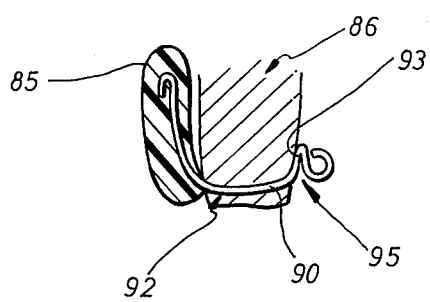
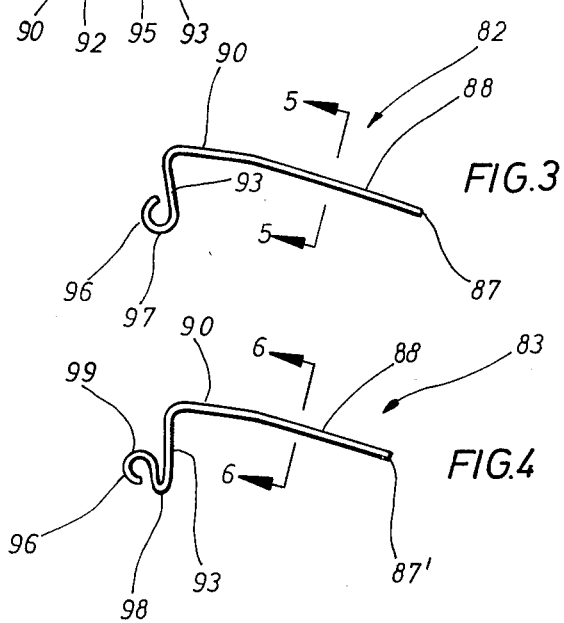
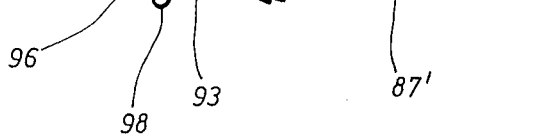

ORTHODONTIC APPLIANCE AND CLASP THEREFOR

BACKGROUND OF THE INVENTION

I. Field of the Invention

The invention relates to an orthodontic appliance for teeth, which is provided with a plurality of clasps, each clasp including a hook and eye portion for removably mounting the appliance in the mouth of a patient.

II. Description of the Prior Art

It has previously been proposed to make orthodontic appliances which include a plurality of clasps, wherein each clasp has an eye portion for receiving an archwire. In order to use such an appliance, additional conventional metal or plastic brackets must be mounted upon the teeth in order to secure the appliance within the mouth of the patient being treated.

A small select group of orthodontic patients object to the use the conventional metal or plastic brackets which must be used in cooperation with the archwire passing through the eye portion of the conventional clasps.

Accordingly, prior to the development of the present invention, there has been no orthodontic appliance, which includes a plurality of clasps, which can be removably mounted within the mouth of a patient, with or without conventional metal or plastic brackets which cooperate with the archwire.

SUMMARY OF THE INVENTION

In accordance with the invention, the foregoing has been achieved through the present orthodontic appliance, which includes a plurality of clasps, each clasp having a hook and eye portion. The clasp of the present invention is bent from a length of orthodontic wire, and comprises a shank portion adapted for positioning in the lingual surface of the orthodontic appliance; an intermediate portion adapted for occupying an occlusal or incisal interproximal space of the teeth; a downwardly depending hook portion attached to said intermediate portion, and bent so as to occupy a labial or buccal interproximal space of the teeth; and an eye portion attached to the hook portion and adapted for receiving an archwire.

A feature of the present invention resides in the fact that the eye portion may be formed by a single or double bend of the orthodontic wire.

The present invention also includes an improvement in orthodontic appliances which comprises a plurality of clasps, each clasp bent from a length of orthodontic wire, disposed in different interproximal sites along the lingual surface of the appliance. Each clasp includes: a shank portion positioned in the lingual surface of the appliance; an intermediate portion for occupying an occlusal or incisal interproximal space of the teeth; a downwardly depending hook portion attached to said intermediate portion, and bent so as to occupy a labial or buccal interproximal space of the teeth; and an eye portion attached to said hook portion, adapted for receiving an archwire.

Another feature of the present invention is that the orthodontic wire used to make the clasps of the present invention may be of either circular or triangular cross-section.

The orthodontic appliance and clasps therefor of the present invention, when compared with previously proposed prior art appliances and clasps has the advantages of: allowing the orthodontic appliance to be removably mounted in the mouth of the patient, whereby the conventional usage of metal or plastic brackets may be eliminated; and efficiency and economy, insofar as the clasps may to a large extent be prefabricated.

BRIEF DESCRIPTION OF THE DRAWINGS

In the drawings:

FIG. 1 is a perspective view of an orthodontic appliance in accordance with the present invention;

FIG. 2 is a perspective view of an orthodontic appliance in accordance with the present invention mounted on the mandible, or lower jaw, of a patient;

FIG. 3 is a plan view of one embodiment of a clasp in accordance with the present invention;

FIG. 4 is a plan view of another embodiment of a clasp in accordance with the present invention;

FIG. 5 is a cross-sectional view of a clasp in accordance with the present invention, taken along line 5—5 of FIG. 3;

FIG. 6 is a cross-sectional view of a clasp in accordance with the present invention, taken along line 6—6 of FIG. 4; and FIG. 7 is a cross-sectional view of the orthodontic appliance and mandible, taken along line 7—7 of FIG. 2.

While the invention will be described in connection with the preferred embodiment, it will be understood that it is not intended to limit the invention to that embodiment. On the contrary, it is intended to cover all alternatives, modifications, and equivalents as may be included within the spirit and scope of the invention as defined by the appended claims.

DETAILED DESCRIPTION OF THE INVENTION

Turning first to FIG. 1, an orthodontic appliance 81 is shown, which includes a plurality of clasps 82 and 83. Appliance 81 may be provided with a suitable archwire 84 which passes through clasps 82 and 83. Appliance 81 is manufactured from any suitable conventional acrylic material 85, and clasps 82 and 83 are embedded in the acrylic material 85 in the following manner.

A conventional impression is made of the patients mandible, shown generally at 86 in FIG. 2, and conventional plaster material is poured into the impression to form a conventional cast (not shown). After separating the cast from the impression, the cast should be trimmed slightly along the lingual surface of each posterior tooth with a sharp Roach carver. Next, a sharp pencil is used to mark the cast where each clasp 82 and 83 will be located, and the sharp Roach carver is used to barely shave away the plaster in the buccalgingival interproximal areas marked by the pencil. A separating medium is painted onto the palatal portion of the cast, but the medium is not painted onto the teeth. Clasps 82 and 83 are then positioned on the lingual surface of the cast, with a small space of clearance in order to permit the acrylic material 85 to flow under each clasp 82 and 83 for adequate fixation. Acrylic material 85 is then poured onto the cast, and before the acrylic material 85 seats, a Roach carver is used to cut away any excess acrylic 85 on the palatal surface and around the lingual surface of the teeth 86. After appliance 81 has been made on the cast, it is carefully separated, trimmed, and highly polished, in a conventional manner.

Turning now to FIG. 2, appliance 81, including clasps 82 and 83, is shown mounted upon the mandible 86 of a patient, archwire 84 not being shown. It should be understood that the appliance 81 and clasps 82 and 83 are likewise suitable for use upon a maxilla, or upper jaw of a human patient as well as upon the mandible 86.

Turning now to FIGS. 3 and 4, the clasps 82 and 83 of the present invention will be described in further detail. Each clasp 82 and 83 is bent from a length of orthodontic wire 87 and 87', which wire may preferably be 0.028 inch orthodontic wire of either a round or triangular cross-section. The length of orthodontic wire 87 and 87' of each clasp 82 and 83 includes a shank portion 88 which is adapted for positioning in the lingual surface 89 (FIG. 2) of appliance 81. Each clasp 82 and 83 also includes an intermediate portion 90 which is adapted for occupying an occlusal or incisal interproximal space of the teeth 86. With reference to FIG. 2, intermediate portion 90 of clasps 82 and 83 is shown to occupy either an occlusal interproximal space 91 between teeth 86, or an incisal interproximal space 92 of teeth 86.

Referring now to FIGS. 3 and 4, clasps 82 and 83 are shown to include a downwardly depending hook portion 93 attached to and integral with intermediate portion 90 of clasps 82 and 83. Hook portions 93 are bent so as to occupy a labial or buccal interproximal space of the teeth. Referring to FIG. 2, hook portion 93 of clasp 82 is shown to occupy buccal interproximal space 94 of teeth 86, and hook portion 93 of clasp 83 is shown to occupy labial interproximal space 95 of teeth 86.

Returning now to FIGS. 3 and 4, it is seen that clasps 82 and 83 each include an eye portion 96, which is adapted to receive an archwire, such as archwire 84 shown in FIG. 1. Clasp 82 of FIG. 3 illustrates an eye portion 96 formed by a single bend 97 of orthodontic wire 87. In FIG. 4, eye portion 96 of clasp 83 is formed by a double bend, 98 and 99 of wire 87'. In both clasps 82 and 83 eye portion 96 may be used to support an archwire, such as that shown at 84 in FIG. 1. Clasp 83, wherein eye portion 96 is formed by double bends 98 and 99 will provide additional rentention than the hook 93 and eye portion 96 of clasp 82 of FIG. 3. Additionally, clasp 83 with double bend 98 and 99 is particularly useful wherein conventional metal or plastic brackets (not shown) will be used in conjunction with clasp 83, whereby eye portion 96 will be sufficiently outwardly spaced from the metal or plastic brackets, to allow archwire 84 to pass through eye portion 96. Preferably the inside dimension of eye portions 96 will be approximately 0.024 inches, which will readily permit passage of any archwire up to 0.022 inches in diameter to pass through eye portion 96.

Turning now to FIG. 5, it is seen that clasp 82 is formed of orthodontic wire 87 having a triangular cross-section. The use of triangular shaped wire is particularly useful insofar as the lower point 100 of wire 87 readily mates with the occlusal 91 or incisal 92 interproximal space of teeth 86, as well as labial 95 or buccal 94 interproximal space of teeth 86.

FIG. 6 illustrates the circular cross-section of orthodontic wire 87' from which clasp 83 is made. It should be readily understood that both clasps 82 and 83 could be made from either orthodontic wire 87 or 87'.

Referring now to FIG. 7, clasp 83 is shown disposed on teeth 86. In particular, intermediate portion 90 is disposed so as to occupy incisal interproximal space 92, with hook portion 93 engaging and occupying labial interproximal space 95 of teeth 86.

With reference to FIGS. 1 and 2, it should be noted that the eye portion 96 of each clasp 82 or 83 are preferably in horizontal alignment, in order to facilitate the lacing of archwire 84 through eye portions 96. Substantial deviation from such horizontal alignment could result in uneven forces being exerted upon archwire 84.

The appliance and clasps of the present invention may be used for the following active (application of an orthodontic force) or inactive applications, depending on whether appliance 81 is used only as a removable appliance, or in conjunction with conventional fixed metal or plastic brackets:

Active Applications

1. Retraction of anterior teeth;
2. Labial movement of anterior teeth;
3. Lingual movement of cuspid and bicuspid teeth;
4. Labial and occlusal movement of impacted teeth;
5. Rotation of teeth;
6. Space closing of teeth;
7. Space opening and rotation of teeth;
8. Leveling of teeth;
9. Uprighting of teeth;
10. Torquing of teeth;
11. Head gear;
12. Palate splinting.

Inactive Applications

1. Retention;
2. Splinting.

The foregoing description of the invention has been directed in primary part to a particular preferred embodiment in accordance with the requirements of the Patent Statutes and for purposes of explanation and illustration. It will be apparent, however, to those skilled in this art that many modifications and changes in the specific clasps and appliance utilizing such clasps may be made without departing from the scope and spirit of the invention.

It is Applicant's intention in the following claims to cover such modifications and variations as fall within the true spirit and scope of the invention.

What is claimed is:

1. An orthodontic appliance for teeth, comprising:
   an inner mouth portion;
   at least one clasp, said clasp bent from a length of orthodontic wire, and said clasp including:
      a shank portion positioned in at least one interproximal site in the lingual surface of the inner mouth portion;
      an intermediate portion for occupying an occlusal or incisal interproximal space in the teeth;
      a downwardly depending hook portion attached to said intermediate portion, and bent so as to occupy a labial or buccal interproximal space of the teeth; and
      an eye portion attached to said hook portion, adapted for receiving an archwire.

2. The orthodontic appliance of claim 1 wherein at least two clasps are positioned on the inner mouth portion and the eye portions of the clasps are in horizontal alignment.

3. The orthodontic appliance of claim 1 wherein the eye portion is formed by a single bend of the orthodontic wire.

4. The orthodontic appliance of claim 1 wherein the eye portion is formed by a double bend of the orthodontic wire.

5. The orthodontic appliance of claim 1 wherein the orthodontic wire is of a circular cross-section.

6. The orthodontic appliance of claim 1 wherein the orthodontic wire is of a triangular cross-section.

* * * * *

UNITED STATES PATENT AND TRADEMARK OFFICE
CERTIFICATE OF CORRECTION

PATENT NO. : 4,273,530
DATED : June 16, 1981
INVENTOR(S) : Garfford J. Broussard It is certified that error appears in the above-identified patent and that said Letters Patent are hereby corrected as shown below:

Column 1, line 20, delete the second occurrence of "the", and before "conventional" insert --of--.

Column 2, line 44, change "patients" to --patient's--.

Column 3, line 40, change "rentention" to --retention--.

Signed and Sealed this

Twenty-second Day of September 1981

[SEAL]

Attest:

GERALD J. MOSSINGHOFF

Attesting Officer

Commissioner of Patents and Trademarks